(12) United States Patent
Carlyon

(10) Patent No.: US 8,540,682 B2
(45) Date of Patent: Sep. 24, 2013

(54) PLUNGER ACTIVATED CAPPING SYSTEM

(75) Inventor: James L. Carlyon, Farmington, MO (US)

(73) Assignee: Covidien LP, Mansfield, MA (US)

( * ) Notice: Subject to any disclaimer, the term of this patent is extended or adjusted under 35 U.S.C. 154(b) by 1044 days.

(21) Appl. No.: 12/409,133

(22) Filed: Mar. 23, 2009

(65) Prior Publication Data

US 2009/0247958 A1 Oct. 1, 2009

Related U.S. Application Data

(60) Provisional application No. 61/040,996, filed on Mar. 31, 2008.

(51) Int. Cl.
*A61M 5/315* (2006.01)

(52) U.S. Cl.
USPC ........... 604/218; 604/110; 604/181; 604/187; 604/533

(58) Field of Classification Search
USPC .......................... 604/110, 181, 187, 533, 218
See application file for complete search history.

(56) References Cited

U.S. PATENT DOCUMENTS

| | | | | |
|---|---|---|---|---|
| 5,735,825 A | * | 4/1998 | Stevens et al. | 604/218 |
| 5,899,887 A | * | 5/1999 | Liu | 604/195 |
| 6,193,687 B1 | * | 2/2001 | Lo | 604/110 |

* cited by examiner

*Primary Examiner* — Kevin C Sirmons
*Assistant Examiner* — Edelmira Bosques
(74) *Attorney, Agent, or Firm* — Lisa E. Winsor, Esq.

(57) ABSTRACT

A plunger activated capping system is disclosed which includes a syringe body defining a fluid reservoir, a plunger assembly including a plunger rod and a sealing member supported on the plunger rod, and a luer cap releasably secured to a distal end of the syringe body. The luer cap includes a luer-type connector member and a fluid outlet. A luer cap plug is releasably supported on a distal end of the plunger rod at a location distally of the sealing member. The luer cap plug is movable into engagement with the luer cap to seal the fluid outlet of the luer cap upon advancement of the plunger assembly from a retracted position to an advanced position. The plunger assembly is configured to effect disengagement of the luer cap from the distal end of the syringe body when the plunger assembly is moved to the advanced position.

20 Claims, 5 Drawing Sheets

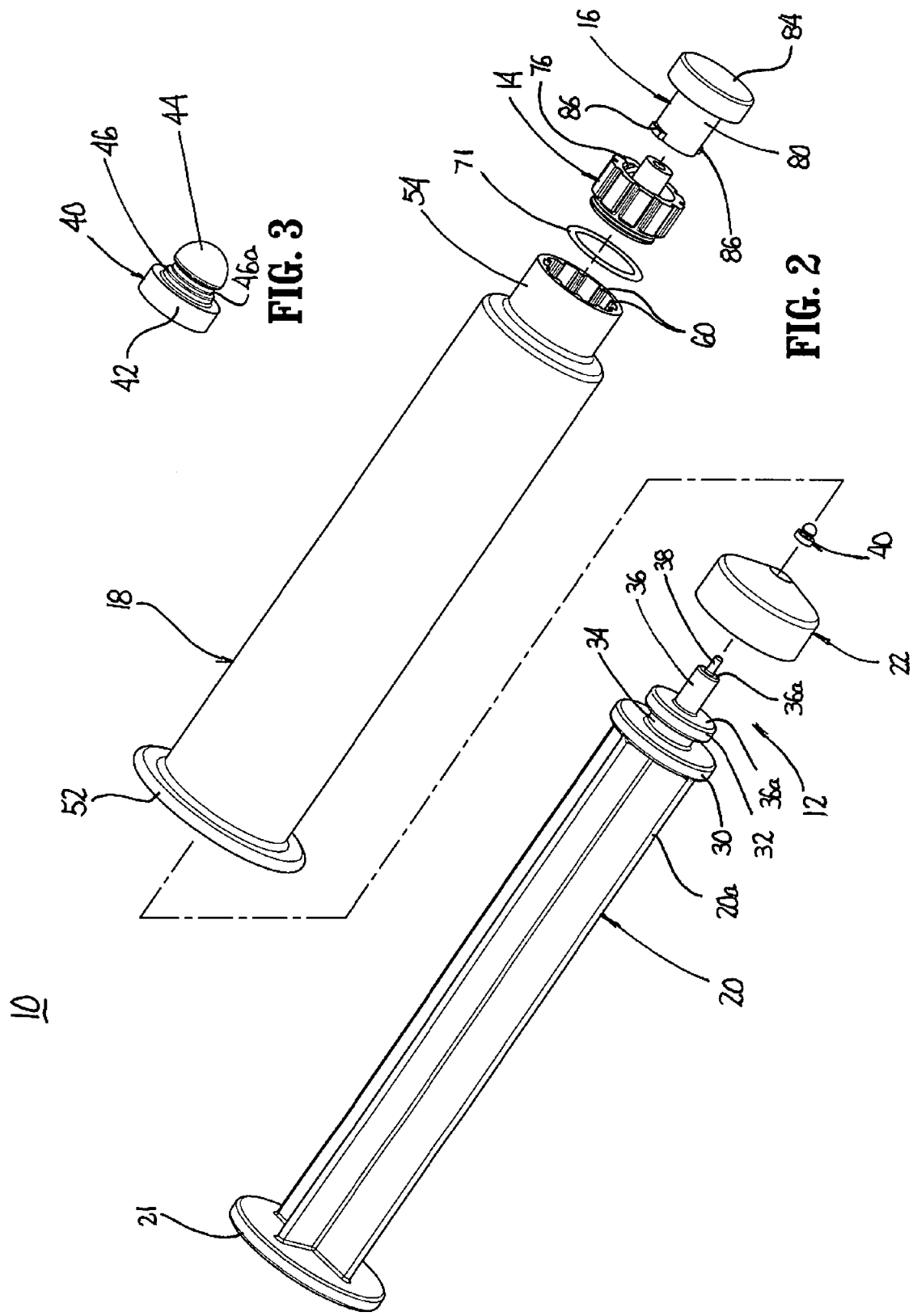

PLUNGER ACTIVATED CAPPING SYSTEM

CROSS REFERENCE TO RELATED APPLICATION

This patent application claims priority to U.S. Provisional Application Ser. No. 61/040,996, filed Mar. 31, 2008, which is incorporated here in its entirety by reference.

BACKGROUND

1. Technical Field

The present disclosure relates to syringes and, more particularly, to a syringe having a luer cap including anti-reflux capabilities for transfer to an indwelling catheter.

2. Background of Related Art

Intravenous or I.V. catheters which are inserted into a patient's vasculature, e.g., vein, to facilitate a variety of different medical procedures, including blood withdrawal, medication delivery, dialysis, etc., over an extended period of time are well known in the art. Such I.V. catheters minimize the pain and discomfort to a patient associated with multiple needle injections which may be required during a hospital stay.

One problem associated with I.V. catheters is that I.V. catheters are susceptible to clotting and may also lead to infection. More particularly, if blood stagnates within the catheter, the blood will eventually clot and occlude the catheter lumen. Further, stagnant blood provides a food source for planktonic bacteria which may form a biofilm and cause infection.

To overcome these problems, systems have been developed for flushing I.V. catheters after fluid has been injected into or removed from the catheter. In one such system, a syringe having a luer connector which is pre-filled with a fluid or lock solution, e.g., saline or heparin, is connected to the I.V. catheter and fluid is dispensed from the syringe to flush any medicament, blood or other fluid from the catheter.

Typically, an I.V. catheter includes a valve structure connected to a proximal end of the catheter which imparts either neutral or positive (distal direction) displacement upon the fluid in the catheter when a syringe is detached from the valve structure. One problem associated with known valve structures is that repeated access increases the potential for introducing bacteria and other microorganisms into the catheter leading to infection. Furthermore, at times, these valve structures don't eliminate the existence of reflux, i.e., fluid or blood being drawn into the distal end of the catheter. As discussed above, reflux may result in clotting of the catheter or infection and is undesirable.

Accordingly, a continuing need exists in the medical arts for a syringe type flush system which can be easily connected to an I.V. catheter assembly, operated in a conventional manner and used as a means for capping or sealing off the proximal end of the catheter without causing reflux, thus obviating the need for reusable valve structures.

SUMMARY

A plunger activated capping system is disclosed which includes a syringe body defining a fluid reservoir, a plunger assembly including a plunger rod and a sealing member supported on the plunger rod, and a luer cap releasably secured to a distal end of the syringe body. The luer cap includes a luer-type connector member and defines a fluid outlet. A luer cap plug is releasably supported on a distal end of the plunger rod at a location distally of the sealing member. The luer cap plug is movable into engagement with the luer cap to seal the fluid outlet of the luer cap upon advancement of the plunger assembly from a retracted position to an advanced position. The plunger assembly is configured to effect disengagement of the luer cap from the distal end of the syringe body when the plunger assembly is moved to the advanced position to provide a cap on an inlet end of an I.V. catheter.

In one embodiment, the distal end of the plunger rod includes a distal extension and the luer cap plug is releasably supported on the distal extension. A finger can be provided on the distal extension which extends distally from the distal extension of the plunger rod such that the luer cap plug is releasably supported on the finger. The luer cap plug can be formed from an elastomeric material and is retained on the finger by friction.

In one embodiment, the syringe body includes a hub portion defining a recess dimensioned to receive the luer cap. The luer cap can be frictionally retained in the recess of the hub portion. An outer surface of the luer cap can include a first plurality of spaced longitudinally extending ribs and an inner surface of the hub portion of the syringe body can include a second plurality of spaced longitudinally extending ribs which define channels dimensioned to slidably receive the first plurality of spaced longitudinally extending ribs to frictionally retain the luer cap within the hub portion of the syringe body.

In one embodiment, the fluid outlet of the luer cap defines a channel having an engagement member formed therein. The luer cap plug is configured to engage the engagement member defined in the channel of the fluid outlet of the luer cap to retain the luer cap plug within the channel when the plunger assembly is moved to the advanced position. The engagement member can include an annular rib formed about the channel to engage the luer cap plug. The luer cap plug can include an annular recess dimensioned to receive the annular rib to secure the luer cap plug within the channel. In one embodiment, the luer cap plug includes a bulbous head positioned distally of the annular recess.

BRIEF DESCRIPTION OF THE DRAWINGS

Various embodiments of the presently disclosed plunger activated capping system are disclosed herein with reference to the drawings, wherein:

FIG. 2 is an exploded, side perspective view of the plunger activated capping system shown in FIG. 1;

FIG. 3 is an enlarged side perspective view of the luer cap plug of the plunger activated capping system shown in FIG. 2;

DETAILED DESCRIPTION OF EMBODIMENTS

Figure 1:
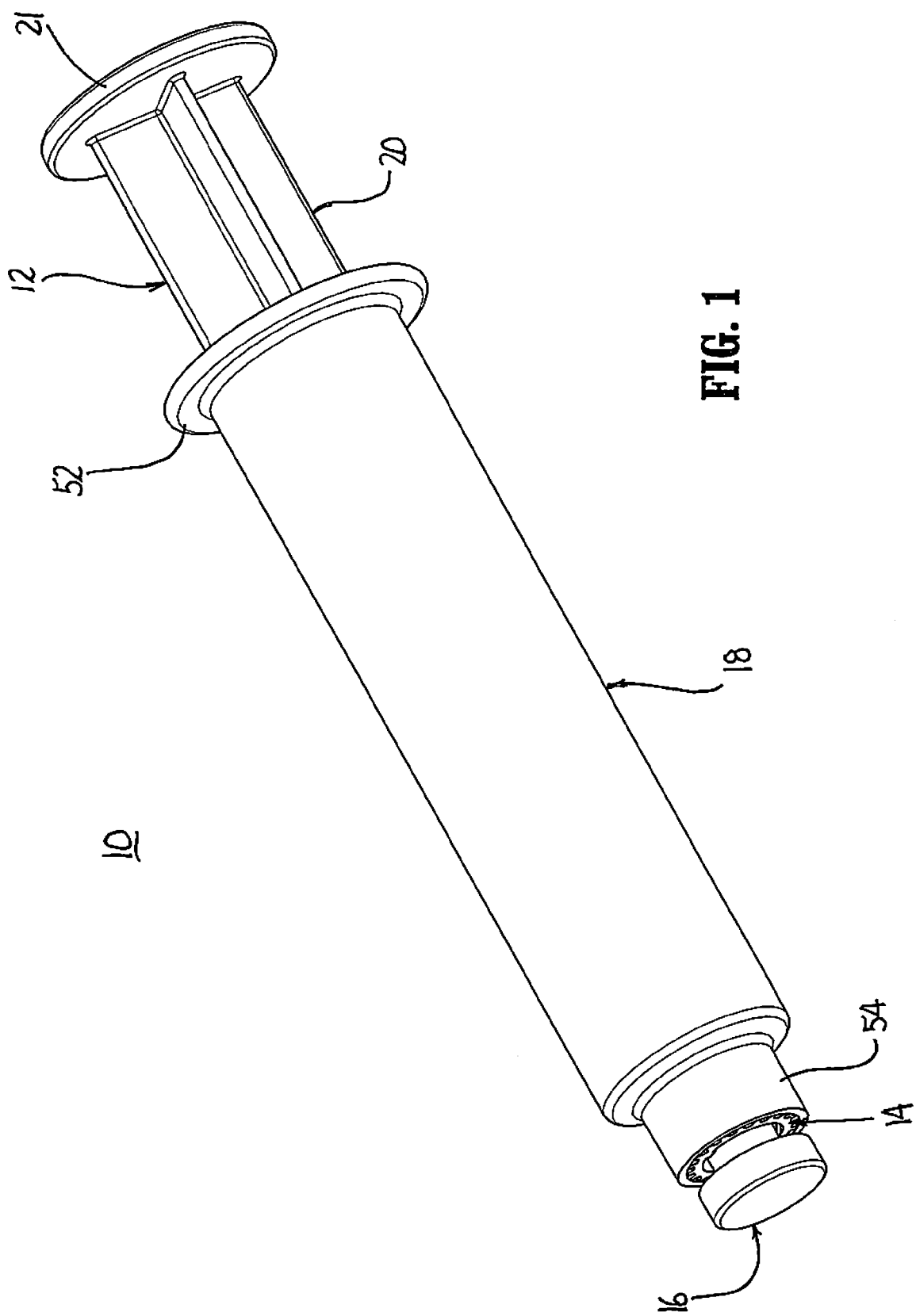
FIG. 1 is a side perspective view of one embodiment of the presently disclosed plunger activated capping system with a sterility cap sealing a distal end of the syringe body.

Embodiments of the presently disclosed plunger activated capping system and its method of use will now be described in detail with reference to the drawings wherein like reference numerals designate identical or corresponding elements in each of the several views. In this description, the term proximal is generally used to indicate the relative nearness of a referenced item to a user of the device and the term distal is used to indicate the relative remoteness of a referenced item to a user of the device.

FIGS. 1 and 2 illustrate one embodiment of the presently disclosed plunger activated capping system shown generally as 10. Briefly, capping system 10 includes a plunger assembly 12, a luer cap 14, a sterility cover 16 and a syringe body 18. Sterility cover 16 is releasably connected to a distal end of luer cap 14, as will be discussed in further detail below, to seal the distal end of syringe body 18 until immediately prior to use of capping system 10.

Figure 4:
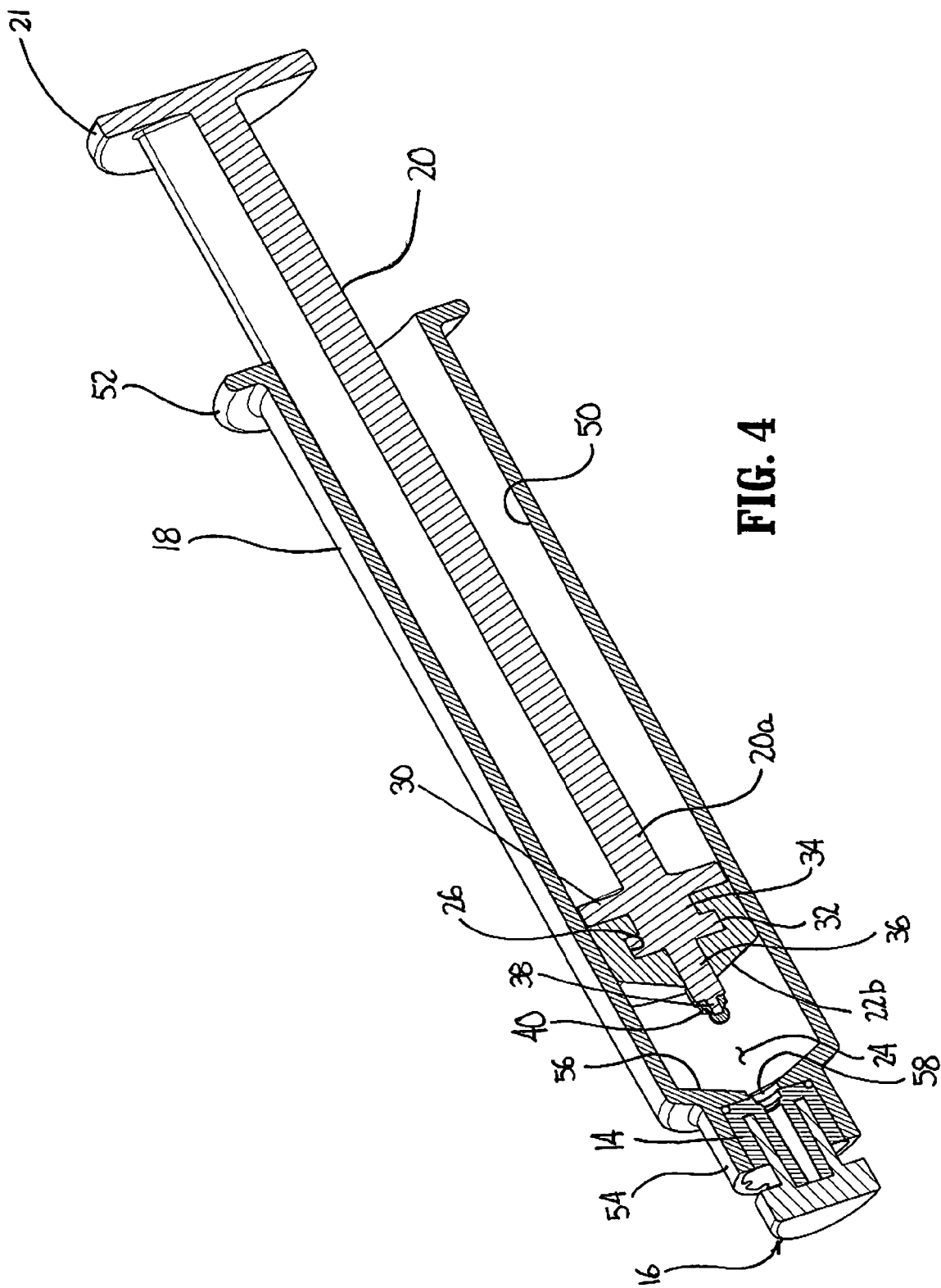
FIG. 4 is a side cross-sectional view of the plunger activated capping system shown in FIG. 1 with the plunger in a retracted position prior to operation of the system.

Referring to FIGS. 1-3, plunger assembly 12 includes a plunger rod 20 and a sealing member 22. Plunger rod 20 includes a proximal finger engagement member 21. Sealing member 22 is supported on a distal end 20a of plunger rod 20 and defines a stepped throughbore 26 (FIG. 4). Distal end 20a of plunger rod 20 includes a large diameter transverse disc portion 30, a small diameter disc portion 32, an intermediate step portion 34 connecting disc portions 30 and 32, and a distal extension 36 which extends from a distal face 32a of disc portion 32 through sealing member 22. A distally extending finger element 38 extends from the distal end of distal extension 36. An interface between distal extension 36 and finger element 38 defines a shoulder 36a.

Referring also to FIG. 4, when sealing member 22 is supported on plunger rod 20, a distal face 30a of disc portion 30 abuts a proximal face 22a of sealing member 22 such that small diameter disc portion 32, intermediate step portion 34 and distal extension 36 are positioned within stepped throughbore 26 of sealing member 22. As illustrated in FIG. 4, when sealing member 22 is secured to distal end 20a of plunger rod 20, distal extension 36 and finger element 38 extend distally from a distal face 22b of sealing member 22.

Referring to FIGS. 2-4, luer cap plug 40 is formed from an elastomeric material and includes a body 42 and a bulbous head 44 which are interconnected by a neck portion 46 (FIG. 3) of reduced diameter. Neck portion 46 defines a recess 46a between body 42 and bulbous head 44. Luer cap plug 40 defines a blind bore 48 (FIG. 6) dimensioned to receive finger element 38 of plunger rod 20 such that luer cap plug 40 is frictionally retained on finger element 38. In one embodiment, luer cap plug 40 is formed from a resilient, deformable material such as an elastomer or rubber, e.g., neoprene. Alternatively, it is envisioned that other materials having similar characteristics may be used to form luer cap plug 40.

Referring to FIGS. 2 and 4, syringe body 18 defines a fluid reservoir 24 which is dimensioned to slidably receive plunger assembly 12 such that sealing member 22 slidably engages an inner wall 50 of syringe body 18. A proximal open end 18a of syringe body 18 includes a gripping flange 52 and a distal end 18b of syringe body 18 includes a cylindrical hub portion 54. A wall 56 formed at the distal end of reservoir 24 defines an outlet opening 58. Cylindrical hub portion 54 defines cavity 54a [not labeled](FIG. 6) dimensioned to releasably receive luer cap 14.

Figure 6:
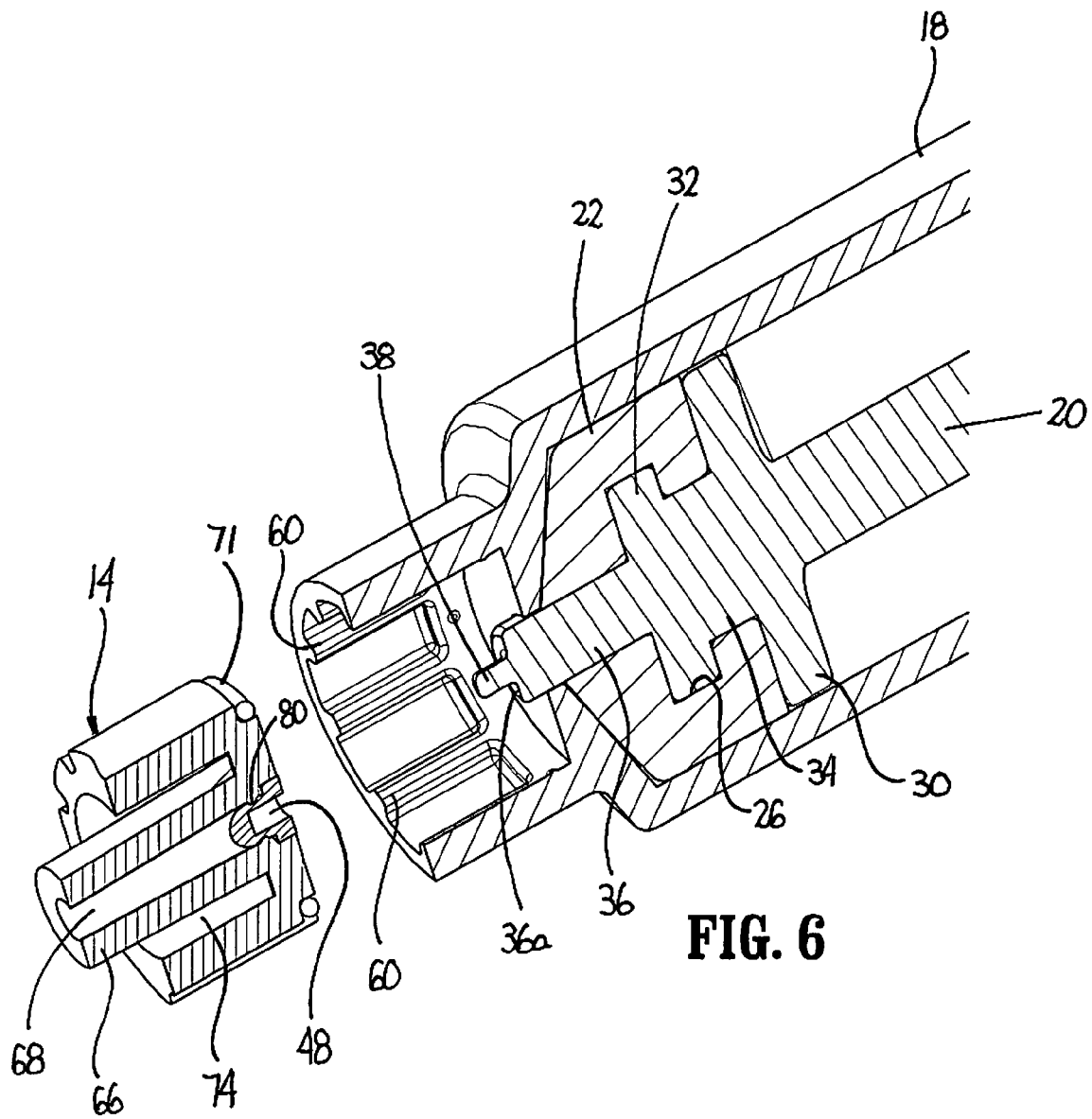
FIG. 6 is an enlarged side cross-sectional view of the distal end of the plunger activated capping system shown in FIG. 5A with the plunger rod fully advanced and the luer cap disengaged from the hub of the syringe body.

Referring to FIGS. 2 and 6, a series of spaced longitudinally extending ribs 60 are positioned about an inner surface of hub portion 54. As will be discussed in further detail below, ribs 60 are configured to releasably retain luer cap 14 within hub portion 54 of syringe body 18 until plunger assembly 12 has been moved to its fully advanced position.

Referring to FIGS. 2 and 6, luer cap 14 includes an outer cylindrical body portion 64 and an inner tapered body portion 66 which defines a fluid outlet or channel 68. The outer surface of outer cylindrical body portion 64 includes a plurality of spaced longitudinally extending ribs 70. Each of ribs 70 is dimensioned to be frictionally retained between a pair of ribs 60 to frictionally retain luer cap 14 within cavity 54a of hub portion 54. Ribs 60 and 70 prevent relative rotation between hub portion 54 and luer cap 14 during securement of capping system 10 to an I.V. or indwelling catheter assembly (not shown). As illustrated, the engaging surfaces of ribs 60 and 70 can be roughened, ribbed, knurled or the like to improve retention of luer cap 14 within cavity 54a of hub portion 54. A sealing member, e.g., an elastic O-ring 71, can be provided between luer cap 14 and an inner wall of hub portion 54 to prevent fluid leakage about hub portion 54. Alternatively, other known sealing members may be used instead of O-ring 71. It is envisioned that luer cap 14 can be retained within hub portion 54 using other known means of retention, e.g., detents, frangible structure, etc. Outer cylindrical body portion 64 and inner tapered body portion 66 define an annular channel 74 (FIG. 6). Body portion 64 includes an internal thread 76 (FIG. 2) which forms a helical-type coupling member. Coupling member 76 is configured to releasably engage a helical coupling member of an I.V. or indwelling catheter assembly (not shown) to secure capping system 10 to the catheter assembly.

Referring again to FIGS. 2 and 4, sterility cover 16 includes a cylindrical body portion 80 and a cover portion 84. A proximal end of body portion 80 includes radially extending projections 86 which form a helical-type coupling member configured to engage coupling member 76 of body portion 64. Projections 86 rotatably engage thread 76 of body portion 64 to rotatably and releasably secure sterility cover 16 to luer cap 14. When cover 16 is secured to body portion 64, cylindrical body portion 80 is positioned in annular channel 74 of luer cap 14 such that fluid outlet 68 is enclosed by cover portion 84 of cover 16.

Referring to FIG. 4, when plunger assembly 12 is in the retracted position, sealing member 22 is spaced from distal wall 56 of syringe body 18 and luer cap plug 40 is spaced from outlet opening 58 in distal wall 56. Prior to use of plunger activated capping system 10, sterility cover 16 can be removed from engagement with luer cap 14 by rotating sterility cover 16 in relation to luer cap 14 to disengage projections 86 of cover 16 from coupling member 76 of luer cap 14. After sterility cover 16 has been removed from luer cap 14 (FIG. 5), if syringe body 12 has been prefilled with a flushing or lock solution, system 10 can be coupled to an indwelling catheter (not shown) by rotatably securing thread 76 to a helical coupling member (not shown) of the indwelling catheter. Alternatively, if syringe body 18 is not prefilled with solution, plunger assembly 12 can be actuated in a conventional manner to draw fluid into reservoir 24.

Figures 5, 5A:
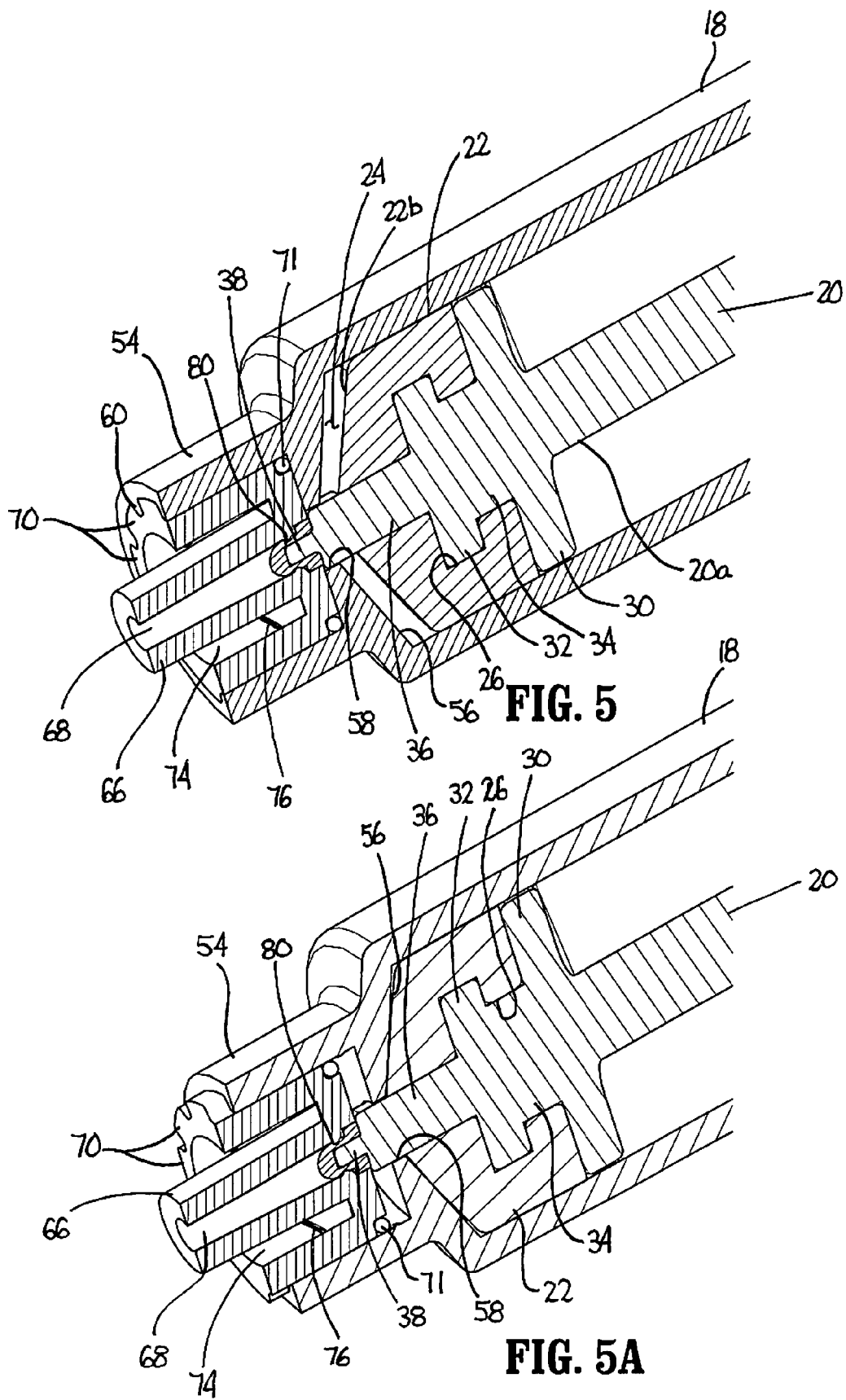
FIG. 5 is an enlarged side, cross-sectional view of the distal end of the plunger activated capping system shown in FIG. 4 with the sterility cap removed and the plunger rod advanced to a position in which the luer cap plug has engaged the luer cap.
FIG. 5A is an enlarged side cross-sectional view of the distal end of the plunger activated capping system shown in FIG. 5 with the plunger rod in the fully advanced position and the luer cap moved partially from within the hub of the syringe body.

Referring to FIG. 5, as plunger assembly 12 is moved toward the advanced position, distally extending finger 38 extends through outlet opening 58 in distal wall 56 of syringe body 18 to position luer cap plug 40 within a proximal end of fluid outlet 68 of luer cap 14. As illustrated in FIG. 5, the wall defining the proximal end of fluid outlet 68 includes an annular rib 80. As bulbous head 44 of luer cap plug 40 engages annular rib 80, bulbous head 44 is easily deformed and passes over annular rib 80 such that annular rib 80 moves into recess 46a (FIG. 3) of neck portion 46 of luer cap plug 14. The force exerted on plunger assembly 12 to position annular rib 80 into recess 46a of neck portion 46 is less than the force required to disengage luer cap 14 from hub portion 54 of syringe body 18 as will be discussed in further detail below. Engagement of rib 80 within recess 46a secures luer cap plug 40 within outlet channel 68 to seal the outlet channel. At this point, shoulder 36a of distal extension 36 is positioned substantially adjacent a proximal face of luer cap 14 and sealing member 22 is nearing distal wall 56 of syringe body 18.

Referring to FIG. 5A, continued movement of plunger assembly 12 towards the advanced position initiates disengagement of luer cap 14 from hub portion 54 of syringe body 18. More specifically, as plunger assembly 12 moves to the fully advanced position, shoulder 36a of distal extension 36 of plunger rod 20 engages the proximal face of luer cap 14 to urge luer cap 14 from within cavity 54a of hub portion 54. Thereafter, when plunger 20 is retracted, finger 38 is pulled from bore 48 of luer cap plug 40 to disengage luer cap plug 40 from plunger 20. Syringe body 18 and plunger assembly 12 can now be disposed of in a safe manner. Luer cap 14 remains fastened to the indwelling catheter with luer cap plug 40 positioned to seal outlet opening 68 of luer cap 14. Since the plugged luer cap 14 (See FIG. 6) remains secured to the indwelling catheter, the removal of syringe body 18 from the indwelling catheter does not cause reflux into the catheter.

It will be understood that various modifications may be made to the embodiments disclosed herein. For example, a variety of different techniques or devices can be used to retain the luer cap within the hub portion of the syringe body including frangible couplings, detents, interlocking components, etc. Further, the luer cap plug can be secured to the plunger using a variety of techniques known in the art. Thus, the distal end of the plunger may assume a variety of configurations not disclosed herein. Therefore, the above description should not be construed as limiting, but merely as exemplifications of preferred embodiments. Those skilled in the art will envision other modifications within the scope and spirit of the claims appended hereto.

What is claimed is:

1. A plunger activated capping system comprising:
   a syringe body defining a fluid reservoir;
   a plunger assembly including a plunger rod and a sealing member supported on the plunger rod;
   a luer cap releasably secured to a distal end of the syringe body, the luer cap including a luer-type connector member and defining a fluid outlet; and
   a luer cap plug releasably supported on a distal end of the plunger rod at a location distally of the sealing member, the luer cap plug being movable into the fluid outlet of the luer cap upon advancement of the plunger assembly from a retracted position to an advanced position to establish a substantial seal within the fluid outlet.

2. The plunger activated capping system according to claim 1, wherein the distal end of the plunger rod includes a distal extension, the luer cap plug being releasably supported on the distal extension.

3. The plunger activated capping system according to claim 2, further including a finger extending distally from the distal extension of the plunger rod, the luer cap plug being releasably supported on the finger.

4. The plunger activated capping system according to claim 3, wherein the luer cap plug is formed from an elastomeric material.

5. The plunger activated capping system according to claim 4, wherein the luer cap plug is retained on the finger by friction.

6. The plunger activated capping system according to claim 1, wherein the syringe body includes a hub portion defining a recess dimensioned to receive the luer cap.

7. The plunger activated capping system according to claim 6, wherein the luer cap is frictionally retained in the recess of the hub portion.

8. The plunger activated capping system according to claim 7, wherein an outer surface of the luer cap includes a first plurality of spaced longitudinally extending ribs.

9. The plunger activated capping system according to claim 8, wherein the inner surface of the hub portion of the syringe body includes a second plurality of spaced longitudinally extending ribs which define channels dimensioned to slidably receive the first plurality of spaced longitudinally extending ribs to frictionally retain the luer cap within the hub portion of the syringe body.

10. The plunger activated capping system according to claim 1, wherein the fluid outlet of the luer cap defines a channel having an engagement member formed therein.

11. The plunger activated capping system assembly according to claim 10, wherein the luer cap plug is configured to engage the engagement member defined in the channel of the fluid outlet of the luer cap to retain the luer cap plug within the channel when the plunger assembly is moved to the advanced position.

12. The plunger activated capping system according to claim 11, wherein the engagement member includes an annular rib formed about the channel to engage the luer cap plug.

13. The plunger activated capping system according to claim 12, wherein the luer cap plug defines an annular recess dimensioned to receive the annular rib to secure the luer cap plug within the channel.

14. The plunger activated capping system according to claim 13, wherein the luer cap plug includes a bulbous head positioned distally of the annular recess.

15. The plunger activated capping system according to claim 1, wherein the plunger assembly is configured to effect disengagement of the luer cap from the distal end of the syringe body when the plunger assembly is moved to the advanced position.

16. The plunger activated capping system according to claim 15, wherein the plunger rod includes a distal extension which is dimensioned to engage the luer cap when the plunger assembly moves towards the advanced position to initiate disengagement of the luer cap from the syringe body.

17. A medical system, which comprises:
   a syringe body defining a fluid reservoir and having an outlet opening;
   a plunger at least partially disposed within the fluid reservoir of the syringe body, the plunger being movable from a retracted position to an advanced position, the plunger having proximal and distal ends;
   a luer cap releasably mounted to the syringe body adjacent the outlet opening thereof, the luer cap defining a fluid outlet in fluid communication with the outlet opening of the syringe body; and
   a luer cap plug releasably supported on the distal end of the plunger, the luer cap plug being movable into the fluid outlet of the luer cap upon advancement of the plunger from the retracted position toward the advanced position to establish a substantial seal within the fluid outlet of the luer cap.

18. The medical system according to claim 17 wherein the plunger is adapted to move to an intermediate position between the retracted position and the advanced position, the luer cap plug being at least partially disposed within the fluid outlet of the luer cap when the plunger is in the intermediate position to establish the substantial seal within the fluid outlet.

19. The medical system according to claim 18 wherein the plunger is dimensioned and configured to initiate disengagement of the luer cap from the syringe body upon movement of the plunger to the advanced position.

20. The medical system according to claim 19 wherein the luer cap plug is dimensioned and configured to be retained within the fluid outlet of the luer cap and released from the plunger subsequent to movement of the plunger to the advanced position.

* * * * *